(12) United States Patent
Gorski

(10) Patent No.: US 10,024,834 B2
(45) Date of Patent: Jul. 17, 2018

(54) DEVICES AND METHODS FOR DETECTING AN EXPLOSIVE SUBSTANCE

(71) Applicant: Bernard Gorski, Sarasota, FL (US)

(72) Inventor: Bernard Gorski, Sarasota, FL (US)

(73) Assignee: Trace Eye-D, LLC, Bradenton, FL (US)

( * ) Notice: Subject to any disclaimer, the term of this patent is extended or adjusted under 35 U.S.C. 154(b) by 0 days.

(21) Appl. No.: 15/492,349

(22) Filed: Apr. 20, 2017

(65) Prior Publication Data

US 2018/0113107 A1 Apr. 26, 2018

Related U.S. Application Data

(63) Continuation-in-part of application No. 15/331,340, filed on Oct. 21, 2016.

(51) Int. Cl.

| | | |
|---|---|---|
| G01N 21/78 | (2006.01) | |
| G01N 21/84 | (2006.01) | |
| G01N 31/22 | (2006.01) | |
| G01N 33/22 | (2006.01) | |
| G01N 25/00 | (2006.01) | |
| G01N 21/29 | (2006.01) | |
| G01N 1/02 | (2006.01) | |
| G01N 33/00 | (2006.01) | |
| G01N 21/77 | (2006.01) | |

(52) U.S. Cl.
CPC ........... *G01N 33/227* (2013.01); *G01N 21/84* (2013.01); *G01N 31/22* (2013.01); *G01N 31/227* (2013.01); *G01N 33/22* (2013.01); *G01N 21/293* (2013.01); *G01N 21/783* (2013.01); *G01N 25/00* (2013.01); *G01N 33/0057* (2013.01); *G01N 2001/022* (2013.01); *G01N 2001/028* (2013.01); *G01N 2021/7759* (2013.01)

(58) Field of Classification Search
CPC ...... G01N 21/78; G01N 31/22; G01N 33/227; G01N 33/22; G01N 2021/7759; G01N 31/227; G01N 33/0057; G01N 2001/022; G01N 2001/028; G01N 21/293; G01N 21/783; G01N 21/84; G01N 25/00
See application file for complete search history.

(56) References Cited

U.S. PATENT DOCUMENTS

| | | | |
|---|---|---|---|
| 4,788,039 A * | 11/1988 | Glattstein | G01N 31/22 252/193 |
| 7,846,740 B2 | 12/2010 | Amisar | |
| 8,377,713 B2 | 2/2013 | Miller et al. | |
| 8,475,717 B2 | 7/2013 | Haas et al. | |
| 8,590,791 B2 | 11/2013 | Haas et al. | |
| 8,641,843 B2 | 2/2014 | Hagit et al. | |
| 8,932,537 B2 | 1/2015 | Haas et al. | |
| 8,969,095 B1 * | 3/2015 | Haas | G01N 31/22 250/339.15 |
| 9,429,523 B2 | 8/2016 | Haber | |
| 9,575,046 B1 * | 2/2017 | Laquidara | G01N 33/227 |
| 2008/0206879 A1 | 8/2008 | Malone et al. | |
| 2009/0029480 A1 * | 1/2009 | Loane | G01N 21/78 436/170 |
| 2012/0003746 A1 | 1/2012 | Amisar | |
| 2012/0184044 A1 | 7/2012 | Kalivretenos et al. | |
| 2013/0130398 A1 | 5/2013 | Zang | |
| 2014/0051173 A1 * | 2/2014 | Barstis | G01N 21/78 436/43 |
| 2014/0127824 A1 | 5/2014 | Amisar | |
| 2014/0193923 A1 | 7/2014 | Zang et al. | |
| 2014/0287520 A1 * | 9/2014 | Ghodousi | G01N 21/78 436/164 |
| 2015/0004710 A1 * | 1/2015 | Gregory | G01N 33/227 436/75 |
| 2015/0260741 A1 | 9/2015 | Haas et al. | |
| 2015/0268171 A1 | 9/2015 | Haber | |
| 2017/0102372 A1 * | 4/2017 | Zussman | G01N 33/227 |

FOREIGN PATENT DOCUMENTS

| | | |
|---|---|---|
| CN | 104655623 A1 | 5/2015 |
| WO | 2010078426 A1 | 7/2010 |
| WO | 2013001534 A1 | 1/2013 |
| WO | 2015177792 A1 | 11/2015 |

OTHER PUBLICATIONS

Raptor Detection Technologies, LLC, "SAVE-T ® WIPE: Substance Activated Fast Evaluation Technology", Brochure, 2011, Wheatley SPRI, LLC.
Western Sydney University, "Guidelines for Use of Peroxide-Forming Chemicals", Brochure, Jul. 2008.
Boston University, "Peroxide Hazards", Brochure.
Glas, Kristjan, "TATP: Countering the Mother of Satan", The Future of Things, retrieved from <http://thefutureofthings.com/3035-tatp-countering-the-mother-of-satan/>.
6th Wave Innovations Corp, "Explosives Detection Products", retrieved from <http://www.6wic.com/explosives-detection.html>.
6th Wave Innovations Corp, "NESTT-TNT", Instruction Manual, retrieved from <http://www.6wic.com/explosives-detection.html>.
6th Wave Innovations Corp, "Explosives Detection Wipes and Sprays", Color Chart and Usage Instructions, retrieved from <http://www.6wic.com/explosives-detection.htm>.

* cited by examiner

*Primary Examiner* — Jennifer Wecker
(74) *Attorney, Agent, or Firm* — Taft Stettinius & Hollister, LLP

(57) ABSTRACT

A wipe for detecting the presence of an explosive substance is composed of an absorbent or adsorbent substrate and a chemical detection solution impregnated within the substrate. In one embodiment the chemical detection solution includes a combination of reagents operable, when contacted with a particular explosive substance to undergo a chemical reaction or a series of chemical reactions to produce a compound having a visible color. In another embodiment, the chemical detection solution includes a redox color indicating agent that is operable to exhibit a color change upon reacting with the explosive substance.

27 Claims, No Drawings

DEVICES AND METHODS FOR DETECTING AN EXPLOSIVE SUBSTANCE

CROSS REFERENCE TO RELATED APPLICATION

This Application is a continuation-in-part of U.S. patent application Ser. No. 15/331,340 filed Oct. 21, 2016, the contents of which are hereby incorporated by reference herein in its entirety.

BACKGROUND OF THE DISCLOSURE

The present invention relates to devices and methods for rapidly detecting an explosive substance, and more particularly to devices and methods configured to chemically detect the presence or absence of an explosive substance on a surface.

The statements in this section merely provide background information related to the present disclosure and should not be construed as constituting prior art.

To ensure the safety of individuals working in various industries, such as the travel, law enforcement and parcel industries; the ability to rapidly identify and detect indicators of explosive materials is extremely important. Examples of indicators of explosive materials include, for example and without limitation, compounds present in pre-detonated explosive materials such as reagents, intermediates and other chemicals used to make explosive materials (collectively referred to as "precursor compounds"); impurities commonly found in precursor compounds or explosive materials; explosive materials themselves; and post-detonated explosive residues such as chemical products and byproducts of an explosion or detonation (such indicators collectively referred to herein as "explosive substances" or, singularly, an "explosive substance"). While various detection techniques have been described over time; these techniques are largely insufficient for a variety of reasons. For instance, certain techniques use colorimetric field detection kits that are designed to produce a colored compound when a liquid media containing a dissolved reagent reacts with a trace explosive substance. While field detection kits are useful, the liquid medium required to conduct the chemical analysis in such systems increases the risk that a hazardous chemical spill, burn or exposure may occur.

In addition to colorimetric testing, dry detection methods involving spectrometric techniques that analyze either trace particles or vapor samples have also been described. For instance, ion mobility spectrometry (IMS) processes can be used to directly analyze a substrate for the presence of an explosive contaminant. While such processes have some advantages, such as increasing sample throughput and eliminating preparation steps, the cumbersome nature of the required testing equipment makes the process inconvenient.

Still other detection techniques have been explored, including the use of electrospun (electro) sprayed and/or dry spun aromatic polymers that measure the amount of fluorescence emitted by the detection substrate, as well as vapor diffusion procedures that require fluorescence sensing techniques, such as by UV light, to detect the presence of the targeted explosive substances.

There remains a need for a convenient and accurate on-site detection system that is able to rapidly detect the presence or absence of an explosive substance without the need for additional detection equipment and/or materials.

The present invention is intended to address these deficiencies within the prior art.

SUMMARY OF THE DISCLOSURE

In accordance with one aspect of the present disclosure, a wipe for detecting the presence of an explosive substance is provided. In accordance with this aspect, the wipe comprises a fibrous substrate (also referred to herein as an absorbent or adsorbent substrate) and a chemical detection solution impregnated into the substrate.

In accordance with certain embodiments, the chemical detection solution includes a combination of reagents operable, when contacted with a particular explosive substance to undergo a chemical reaction or a series of chemical reactions to produce a compound having a visible color. In one specific embodiment, useful for the detection of nitrate esters, nitroamines and other nitrogen-based explosive substances, the combination of reagents includes Griess reagents. As used herein, the term "Griess reagents" is used to refer to reagents operable to perform a Griess test, which is an analytical chemistry test for detecting the presence of a nitrite ion.

In other embodiments the chemical detection solution includes a redox color indicating agent (also referred to herein as an internal redox indicator) that is configured to exhibit a color change when the solution contacts a particular explosive substance. In one embodiment, the internal redox indicator is a pH independent redox indicator. In another embodiment, the internal redox indicator is a pH dependent redox indicator. In alternative embodiments, the internal redox indicator is substituted with a colored inorganic oxidant or a colored inorganic reductant. In one specific embodiment, useful for the detection of hydrogen peroxide, the internal redox indicator comprises diphenylamine.

The fibrous substrate can take a wide variety of forms, provided that the substrate is operable to absorb, adsorb or otherwise become impregnated with the chemical detection solution. The fibrous substrate in preferred embodiments has a light color so that a color change of the chemical detection solution is readily visible and most preferably is white or nearly white in color. According to certain embodiments herein, the fibrous substrate comprises a plurality of fibers that are selected from the group consisting of cellulose, polyamides, polyesters, polyethylenes, polypropylenes, polyacrylics, cellulose acetate, polylactic acid, silk, wool, glass, polyaramids, and combinations thereof.

In accordance with still other embodiments, the fibrous substrate is a nonwoven material that has multiple layers formed from fibers selected from the group consisting of polyolefin, polypropylene, polyethylene, ethylene copolymers and propylene copolymers.

According to yet still other embodiments, the fibrous substrate is an absorbent nonwoven material that is formed from a blend of spunbond fibers selected from the group consisting of polypropylene, polyester and wood pulp.

In one embodiment, the chemical detection solution comprises a carrier fluid and a combination of reagents operable to undergo a chemical reaction or a series of chemical reactions to produce a compound having a visible color when the solution contacts the explosive substance. In one embodiment, the combination of reagents includes Griess reagents. In another embodiment, the Griess reagents include sulfanilamide and an ethylenediamine dihydrocholoride compound. In one embodiment, the ethylenediamine dihydrocholoride compound comprises ethylenediamine dihydrocholoride. In another embodiment, the ethylenediamine dihydrocholoride compound comprises N-(1-naphthyl)ethylenediamine dihydrochloride. It is not intended, however, that the present disclosure be limited to these specific compounds, a variety of alternate ethylenediamine dihydrocholoride compounds being known and readily available.

In another embodiment the carrier fluid has an acidic pH. In yet other embodiments, the carrier fluid has a pH of from about 2.5 to about 5.0 or from about 3.0 to about 4.5 or from about 3.5 to about 4.0 or about 3.75. In still another embodiment, the carrier fluid includes an acidic aqueous fluid and at least one organic solvent. In still yet another embodiment, the acidic aqueous fluid includes phosphoric acid. In another embodiment, the at least one organic solvent includes dimethyl sulfoxide. It is not intended, however, that the present disclosure be limited to this specific organic solvent, a variety of alternate organic solvents being well known and readily available. For example, and without limitation, another organic solvent contemplated by this disclosure includes acetone. In another embodiment, the carrier fluid includes an alcohol. In yet another embodiment, the alcohol comprises methanol. It is not intended, however, that the present disclosure be limited to this specific alcohol, a variety of alternate alcohols being well known and readily available. For example, and without limitation, another alcohol contemplated by this disclosure includes ethanol. In another embodiment, the carrier fluid includes a base. In one embodiment, the base comprises tetrabutylammonium hydroxide (TBAH). It is not intended, however, that the present disclosure be limited to this specific base, a variety of alternate bases, including bases having similar strengths to TBAH, being well known and readily available.

In one embodiment, the chemical detection solution includes dimethyl sulfoxide, methanol, TBAH, sulfanilamide, ethylenediamine dihydrochloride and phosphoric acid. In another embodiment, the chemical detection solution includes from about 65% to about 85% dimethyl sulfoxide, from about 5% to about 13% methanol, from about 1% to about 5% TBAH, from about 3% to about 9% sulfanilamide, from about 0.1% to about 0.3% ethylenediamine dihydrochloride and from about 5% to about 10% phosphoric acid, all by weight.

In another embodiment, the chemical detection solution comprises a carrier fluid, a redox color indicating agent having a first reduction potential and at least one member of a redox pair having a second reduction potential. In another embodiment, the first reduction potential and the second reduction potential sufficiently correlate to one another to enable the redox color indicating agent to produce a color change when the solution contacts a particular explosive substance (referred to herein as "correlated reduction potentials"). In one embodiment, the carrier fluid has an acidic pH. In another embodiment, the carrier fluid has a pH of from 0 to about 3.5. In yet another embodiment, the carrier fluid has a pH of from about 0.5 to about 1.5. In still another embodiment, the carrier fluid includes an acidic aqueous fluid and at least one organic solvent. In still yet another embodiment, the acidic aqueous fluid includes hydrochloric acid and sulfuric acid. It is not intended, however, that the present disclosure be limited to these specific acids, a variety of alternate acidic fluids being well known and readily available. In still another embodiment, the at least one organic solvent includes dimethyl sulfoxide, isopropyl alcohol and dipropylene glycol dimethylether. It is not intended, however, that the present disclosure be limited to these specific organic solvents, a variety of alternate organic solvents being well known and readily available. In still another embodiment, the redox color indicating agent includes diphenylamine and the at least one member of a redox pair includes ferric ions, which can be provided in the solution, for example, in the form of ferric chloride.

In one embodiment, the chemical detection solution is formed from a first solution that includes dimethyl sulfoxide, isopropyl alcohol, diphenylamine and sulfuric acid and a second solution that includes dipropylene glycol dimethyl ether, ferric chloride and hydrochloric acid. In one embodiment, the first solution and the second solution are combined in a volumetric ratio of from about 2:1 to about 1:2 to provide a final solution, which is the chemical detection solution. In yet another embodiment, the chemical detection solution is formed from a first solution that includes from about 6% to about 9% dimethyl sulfoxide, from about 4% to about 8% isopropyl alcohol, from about 0.1% to about 2% diphenylamine and from about 80% to about 90% sulfuric acid (50% solution), all by weight, and a second solution that includes from about 95% to about 99% dipropylene glycol dimethyl ether, from about 0.1% to about 1.5% ferric chloride and from about 0.01% to about 0.5% hydrochloric acid (30% solution), all by weight. In still another embodiment, the chemical detection solution is formed from a first solution that includes about 7.4% dimethyl sulfoxide, about 6.0% isopropyl alcohol, about 0.5% diphenylamine and about 86.0% sulfuric acid (50% solution), all by weight, and a second solution that includes about 98.4% dipropylene glycol dimethyl ether, about 0.8% ferric chloride and about 0.073% hydrochloric acid (30% solution), all by weight.

A person of ordinary skill in the art will appreciate from the present disclosure that the proportions of the components or ingredients of the chemical detection solution disclosed herein can be varied beyond the example proportions set forth herein and that such variations can impact the speed with which the color-emitting compound is produced or the redox color indicating agent exhibits a color change when it comes into contact with the explosive substance, the amount or concentration of explosive substance required to produce a visible color change within the detection device or other property of the device.

In one embodiment, a wipe for detecting the presence of an explosive substance comprises an absorbent nonwoven fibrous substrate that is formed from a blend of spunbond fibers selected from the group consisting of polypropylene, polyester and wood pulp, and a chemical detection solution impregnated into the substrate. In one embodiment, the chemical detection solution includes a carrier fluid and a combination of reagents operable to undergo a chemical reaction or a series of chemical reactions to produce a compound having a visible color when the solution contacts the explosive substance. The combination of reagents can include, for example, Griess reagents. In another embodiment, the chemical detection solution includes a redox color indicating agent that comprises diphenylamine. In yet another embodiment, the chemical detection solution including a redox color indicating agent further includes dimethyl sulfoxide, isopropyl alcohol, sulfuric acid, dipropylene glycol dimethyl ether, ferric chloride and hydrochloric acid.

In another aspect, the present disclosure provides a method of fabricating an explosive substance detection wipe that comprises (i) providing a chemical detection solution that includes a carrier fluid and Griess reagents, (ii) providing a fibrous substrate, and (iii) impregnating the fibrous substrate with the chemical detection solution to provide an impregnated substrate. In one embodiment, the method further includes placing the impregnated substrate in a sealed package. In one embodiment of the method, the chemical detection solution includes a carrier fluid and a combination of reagents operable to undergo a chemical reaction or a series of chemical reactions to produce a compound having a visible color when the solution contacts the explosive substance.

In one embodiment of this method, the Griess reagents include sulfanilamide and an ethylenediamine dihydrocholoride compound. In one embodiment, the ethylenediamine dihydrocholoride compound comprises ethylenediamine dihydrocholoride. In another embodiment, the ethylenediamine dihydrocholoride compound comprises N-(1-naphthyl)ethylenediamine dihydrochloride. It is not intended, however, that the present disclosure be limited to these specific compounds, a variety of alternate ethylenediamine dihydrocholoride compounds being known and readily available. In another embodiment the carrier fluid has an acidic pH. In yet other embodiments, the carrier fluid has a pH of from about 2.5 to about 5.0 or from about 3.0 to about 4.5 or from about 3.5 to about 4.0 or about 3.75. In still another embodiment, the carrier fluid includes an acidic aqueous fluid and at least one organic solvent. In still yet another embodiment, the acidic aqueous fluid includes phosphoric acid. In another embodiment, the at least one organic solvent includes dimethyl sulfoxide. It is not intended, however, that the present disclosure be limited to this specific organic solvent, a variety of alternate organic solvents being well known and readily available. In another embodiment, the carrier fluid includes an alcohol. In yet another embodiment, the alcohol comprises methanol. It is not intended, however, that the present disclosure be limited to this specific alcohol, a variety of alternate alcohols being well known and readily available. In another embodiment, the carrier fluid includes a base. In one embodiment, the base comprises tetrabutylammonium hydroxide (TBAH). It is not intended, however, that the present disclosure be limited to this specific base, a variety of alternate bases being well known and readily available. In one embodiment, the chemical detection solution includes dimethyl sulfoxide, methanol, TBAH, sulfanilamide, ethylenediamine dihydrochloride and phosphoric acid. In another embodiment, the chemical detection solution includes from about 65% to about 85% dimethyl sulfoxide, from about 5% to about 13% methanol, from about 1% to about 5% TBAH, from about 3% to about 9% sulfanilamide, from about 0.1% to about 0.3% ethylenediamine dihydrochloride and from about 5% to about 10% phosphoric acid, all by weight.

In another aspect, the present disclosure provides a method of fabricating an explosive substance detection wipe that comprises (i) providing a chemical detection solution that includes a carrier fluid, a redox color indicating agent having a first reduction potential and at least one member of a redox pair having a second reduction potential, (ii) providing a fibrous substrate, and (iii) impregnating the fibrous substrate with the chemical detection solution. In one embodiment, the method further includes placing the impregnated substrate in a sealed package. In another embodiment, the first reduction potential and the second reduction potential sufficiently correlate to one another to enable the redox color indicating agent to produce a color change when the solution contacts a particular explosive substance.

In one embodiment of this method, the carrier fluid has an acidic pH. In another embodiment, the carrier fluid has a pH of from 0 to about 3.5. In yet another embodiment, the carrier fluid has a pH of from about 0.5 to about 1.5. In still another embodiment, the carrier fluid includes an acidic aqueous fluid and at least one organic solvent. In still yet another embodiment, the acidic aqueous fluid includes hydrochloric acid and sulfuric acid. It is not intended, however, that the present disclosure be limited to these specific acids, a variety of alternate acidic fluids being well known and readily available. In still another embodiment, the at least one organic solvent includes dimethyl sulfoxide, isopropyl alcohol and dipropylene glycol dimethylether. It is not intended, however, that the present disclosure be limited to these specific organic solvents, a variety of alternate organic solvents being well known and readily available. In still another embodiment, the redox color indicating agent includes diphenylamine and the at least one member of a redox pair includes ferric ions, which can be provided in the solution, for example, in the form of ferric chloride.

In one embodiment, the method includes (i) providing a first solution including dimethyl sulfoxide, isopropyl alcohol, diphenylamine and sulfuric acid, (ii) providing a second solution including dipropylene glycol dimethyl ether, ferric chloride and hydrochloric acid, (iii) combining, at a volumetric ratio of from about 2:1 to about 1:2, the first solution with the second solution to form a chemical detection solution, (iv) providing a fibrous substrate, and (v) impregnating the fibrous substrate with the chemical detection solution. In one embodiment, the method further includes placing the impregnated substrate in a sealed package. In another embodiment of the method, the first solution comprises about 7.4% dimethyl sulfoxide, about 6.0% isopropyl alcohol, about 0.5% diphenylamine and about 86.0% sulfuric acid; and the second solution comprises about 98.4% dipropylene glycol dimethyl ether, about 0.8% ferric chloride and about 0.073% hydrochloric acid.

According to certain embodiments of the method, the fibrous substrate comprises nonwoven material having multiple layers formed from one or more of polyolefin, polypropylene, polyethylene, ethylene copolymers and propylene copolymers. According to other embodiments, the fibrous substrate comprises an absorbent nonwoven material formed from a blend of spunbond fibers selected from the group consisting of polypropylene, polyester and wood pulp.

In another aspect of the disclosure, there is provided a method of determining whether an explosive substance is present on a surface. The method includes (i) providing a detection wipe fabricated from a fibrous substrate impregnated with a chemical detection solution as disclosed herein, (ii) contacting the detection wipe with the surface, (iii) observing whether the detection wipe exhibits a change in color, and (iv) determining whether the explosive substance is present on the surface based on whether the detection wipe exhibits a color change. In one embodiment, the chemical detection solution includes a combination of reagents operable, when contacted with the explosive substance to undergo a chemical reaction or a series of chemical reactions to produce a compound having a visible color. In another embodiment, the chemical detection solution includes a redox color indicating agent operable to change color when contacted with the explosive substance.

In yet another aspect of the disclosure, a method of determining whether an explosive substance is present on a surface includes (i) providing a detection wipe fabricated from a fibrous substrate, (ii) contacting the detection wipe with the surface, (iii) spraying a chemical detection solution as disclosed herein onto the wipe, (iv) observing whether the detection wipe exhibits a change in color, and (v) determining whether the explosive substance is present on the surface based on whether the detection wipe exhibits a color change.

In one embodiment, the chemical detection solution includes a combination of reagents operable, when contacted with the explosive substance to undergo a chemical reaction or a series of chemical reactions to produce a compound having a visible color. In another embodiment, the chemical detection solution includes a redox color indicating agent operable to change color when contacted with the explosive substance.

In various embodiments of the method, the fibrous substrate and the chemical detection solution have features and characteristics as described herein.

Still other features, characteristics, objects and benefits of the disclosure will become apparent from the following description.

DETAILED DESCRIPTION

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Moreover, it should be understood that when certain values and ranges are recited herein in connection with various embodiments of the present teachings, all values and ranges which fall between such listed values and ranges are intended to be encompassed by the present teaching unless explicitly stated otherwise. Finally, although specific methods and materials are described herein with respect to certain exemplary aspects of the present teachings, it should be understood and appreciated that other methods and materials similar or equivalent to those described herein can be used in the practice or testing of the present application without straying from the invention's intended scope.

As will be explained herein, the present disclosure provides devices that include a chemical detection solution impregnated in a substrate, the chemical detection solution operable to selectively react or interact with and visibly identify trace and bulk amounts of explosive substances. In accordance with certain aspects herein, the substrate is in the form of a wipe that is packaged as a single unit for individual use. In other embodiments, multiple wipes are packaged together and can be packaged, for example, in a container operable to dispense wipes individually for use, if desired, a wide variety of which are commercially available.

The substrate can be fabricated from any suitable absorbent or adsorbent material, such as a textile material comprising a plurality of yarns provided in a knit or woven construction or a plurality of fibers that are provided in a non-woven construction. The fibrous substrate can take a wide variety of forms, provided that the substrate is operable to absorb, adsorb or otherwise become impregnated with the chemical detection solution. For example, the fibrous substrate can be of the type commonly used in Kimwipes™ products (Kimberly-Clark), Clorox® wipe products (The Clorox Company), baby wipe products, paper towel products and the like. The fibrous substrate in preferred embodiments has a light color so that a color change of the chemical detection solution is readily visible, and most preferably the fibrous substrate is white or nearly white in color. Suitable fibers include, but are not limited to, cellulose (e.g., cotton and rayon), polyamides, polyesters, polyethylenes, polypropylenes, polyacrylics, cellulose acetate, polylactic acid, silk, wool, glass, polyaramids, and combinations thereof. In specific illustrative embodiments, the substrate comprises an absorbent nonwoven material, such as a bonded and carded material, a spunbonded material, or a meltblown material including meltblown microfibers. In accordance with certain aspects herein, the nonwoven material may also have multiple layers such as, for example, multiple spunbonded layers and/or multiple meltblown layers. Moreover, the nonwoven material may be made of polymers such as, for example, polyolefins, which are intended to include polypropylene, polyethylene, ethylene copolymers and propylene copolymers. According to certain embodiments, the nonwoven material may be an elastic nonwoven material, while in accordance with other embodiments a non-elastic nonwoven material or an extensible nonwoven material may be used.

In one representative embodiment, the substrate is composed of a blend of spunbonded polypropylene, polyester and wood pulp. In one embodiment, the substrate comprises an absorbent nonwoven material including from about 15% to about 35% spunbonded polypropylene, from about 10% to about 30% polyester and from about 40% to about 60% wood pulp, all by weight. In another embodiment, the substrate comprises an absorbent nonwoven material including from about 22% to about 32% spunbonded polypropylene, from about 17% to about 27% polyester and from about 46% to about 56% wood pulp, all by weight. In yet another embodiment, the absorbent nonwoven material may comprise about 26.7% spunbonded polypropylene, about 22.2% polyester and about 51.1% wood pulp, all by weight. As those of skill in the art will understand and appreciate, the production of fibrous layers by means of spunbonding is based on the direct spinning of polymeric granulates into continuous filaments and subsequently manufacturing the fibrous layer. Spunbond fabrics are produced by depositing extruded, spun fibers onto a moving belt in a uniform random manner followed by thermal bonding the fibers. The fibers are separated during the web-laying process by air jets, and fiber bonds are generated by applying heated rolls or hot needles to partially melt the polymer and fuse the fibers together. Since molecular orientation increases the melting point, fibers that are not highly drawn can be used as thermal binding fibers, and polyethylene or random ethylene/-propylene copolymers can be used as low melting bonding sites.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" includes all possible geometrical configurations of the material. These configurations include, but are not limited to, isotactic, syndiaotactic and random symmetries.

To detect the presence or absence of an explosive substance on the surface of an object, the device is contacted with the surface and, if the explosive substance is present, the chemical detection solution impregnated within the substrate reacts or interacts with the material and produces a color change that can be visibly observed by the user without the need for special equipment (e.g., a spectrometer) or the aid of an intervening processing step (e.g., conversion of color change into an electronic signal that is processed by an interpreting device).

To cause the color change to occur, in certain embodiments, the chemical detection solution includes a combination of reagents operable, when contacted with a particular explosive substance to undergo a chemical reaction or a series of chemical reactions to produce a compound having a visible color. As those of skill in the art will understand and appreciate, a variety of reagents can be employed to undergo a chemical reaction or a series of chemical reactions to produce a compound having a visible color when contacted with a particular explosive substance. In one embodiment, the combination of reagents include Griess reagents. As used herein, the term "Griess reagents" refers to reagents operable to perform a Griess test, which is an analytical chemistry test for detecting the presence of a nitrite ion, as described further below. In the presence of nitrite ions, the Griess reagents and the nitrite ion undergo a series of reactions that ultimately produce a compound having visible color, such as an azo dye. While Griess reagents can be used to detect a variety of nitrate ester compounds and nitroamine compounds, a person of ordinary skill in the art will recognize that the chemical detection solution according to this embodiment must also operate to either isolate nitrite ions from the nitrate ester compounds and/or nitroamine compounds, so that the Griess reagents and the nitrite ions can interact to produce the compound having visible color, or react with nitro functional groups of the nitrate ester compounds, nitroamine compounds or other nitro compounds, for example, to convert sulfanilamide to a diazonium salt. The formulations disclosed herein have been found to have excellent detection properties for a wide variety of nitrate esters, nitroamines and other nitro compounds that are known to be explosive compounds and/or to be byproducts of explosions of nitrogen-based explosive materials.

Thus, in one useful application of the disclosed invention, the explosive substances being detected are nitrogen based explosives. As used herein, the term "nitrogen based explosives" refers to explosive materials, compounds used to make explosive materials and products of detonation of explosive materials that include nitrate ester moieties, nitroamine moieties and/or other nitro groups (referred to herein as "nitrate ester compounds," "nitroamine compounds" and "other nitro compounds," respectively). The formulations disclosed herein are operable to interact with nitrite ions released from the nitrate ester compound, nitroamine compound or other nitro compound upon contact with a chemical detection solution as contemplated by the present disclosure or, in some instances, to interact with a nitro functional group of certain compounds. Examples of nitrate ester compounds include, without limitation, nitroglycerin, nitrocellulose (including guncotton), erythritol tetranitrate (ETN) and pentaerythritol tetranitrate (PETN). Examples of nitroamine compounds include, without limitation, FEMX and RDX. An example of an other nitro compound includes, without limitation, trinitrotoluene (TNT). Examples of products that include combinations of these nitrogen based explosive include, without limitation, Semtex, which is a combination of RDX and PETIT, and Comp B, which is a combination of RDX and TNT.

As will be explained in more detail below in connection with certain embodiments, if the user determines that no color change has occurred, he or she can conclude that the targeted explosive substance is not present on the surface that has been tested. On the other hand, if a color change is observed by the user, then a determination can be made that the targeted explosive substance has been positively identified as being present on the surface.

To cause the color change to occur in other embodiments, the chemical detection solution includes a redox color indicator that is configured to change color when the solution comes into contact with the explosive substance (if present). As those of skill in the art will understand and appreciate, redox color indicating agents are intended to refer to those materials that can undergo a redox reaction, and thereby change color, when exposed to appropriate conditions. In the present disclosure, such conditions arise when reagents in the solution come into contact with a targeted explosive substance. As a result of the redox reaction, the redox color indicating agents exhibit a color change. Examples of redox color indicators that are contemplated in accordance with various embodiments of the present disclosure include, but are not limited to, neutral red, amino black, safranine T or O, indigo, indigo carmine, methylene blue, thionine, thymolindophenol, gallocyanine, nile blue, variamine blue, diphenylamine, 2,6-dichlorophenolindophenol, diphenylamine-4-sulfonic acid, barium salt, tris(2,2-dipyridyl)iron(II)sulfate, N-phenylanthranilic acid, ferroin, nitroferroin, 5,6-dimethylferroin, 4-amino-4'-methyldiphenylamine, diphenylbenzindine-disulfonic acid, o-dianisidine, 3,3'-dimethylnaphthidine, 3,3'-dimethylnaphthidine disulfonic acid, bis(5-bromo-1,10-phenanthroline) ruthenium(II)dinitrate, tris(5-nitro-1,10-phenanthroline)iron (II)sulfate, Iron(II)-2,2',2"-tripyridine sulfate, tris(4,7-biphenyl-1,10-phenanthroline)iron(II)disulfate, o,m'-diphenylaminedicarboxylic acid setopaline, p-nitrodiphenylamine, tris(1,10-phenanthroline)-iron(II) sulfate, setoglaucine O, xylene cyanole FF, erioglaucine A, eriogreen, tris(2,2"-bipyridine)-iron(II)hydrochloride, 2-carboxydiphenylamine[N-phenyl-anthranillic acid], benzidine dihydrochloride, o-toluidine, bis(1,10-phenanthroline)-osmium(II)perchlorate, diphenylamine-4-sulfonate Na salt), 3,3'-dimethoxybenzidine dihydrochloride[o-dianisidine], ferrocyphen, 4'-ethoxy-2,4-diaminoazobenzene, N,N-diphenylbenzidine, diphenylamine, N,N-dimethyl-p-phenylenediamine, variamine blue B hydrochloride, N-phenyl-1,2,4-benzenetriamine, bindschedler's green, 2,6-dichloroindophenol (Na salt), 2,6-dibromophenolindophenol, brilliant cresyl blue [3-amino-9-dimethyl-amino-10-methylphenoxyazine chloride], Iron(II)-tetrapyridine chloride, starch (soluble potato, $I_3$ present), gallocyanine (25° C.), nile blue A [aminonaphthodiethyl-amino-phenoxazine sulfate], Indigo-5,5',7,7'-tetrasulfonic acid Na salt), Indigo-5,5',7-trisulfonic acid (Na salt), Indigo-5,5'-disulfonic acid (Na salt), phenosatranine, indigo-5-monosulfonic acid (Na salt), bis(dimethylglyoximato)iron (II)chloride, Induline scarlet, and the like.

As utilized herein, "color change" or "change in color" refers to a change in light absorption, reflection, or fluorescence which can be observed visually or with the help of a simple instrument. The term "light" refers to electromagnetic radiation in ultraviolet, visible, near infrared and infrared wavelength ranges.

In accordance with certain exemplary illustrations herein, the substrate can come in several forms, including, but not limited to, tissues, pads, cloths, sheets, wipes, and towelettes. Moreover, the chemical detection solution is composed of a formulation that is designed to molecularly react or interact with a specific targeted detection substance or group of substances. For instance, in accordance with certain aspects herein, the substrate can be impregnated with a specific chemical formulation that is designed to interact with specific explosive materials, such as a residue of nitrogen based explosive materials or a residue of peroxide based explosive materials. Examples of explosive materials that are intended to be included by the various methods and techniques of the present teachings include, but are not necessarily limited to, TATP, HMTD, TNB, TNP, TNT, Tetryl, Urea, Ammonium Nitrate, Potassium Chlorate, Potassium Perchlorate, Sodium Perchlorate, RDX, PSTN, COMP B & C, ETN, Semtex, and guncotton as well as most gun powders.

The present disclosure contemplates a wide variety of methods to add the solution to the substrate to form a detection device as disclosed herein. One embodiment of the method includes (i) providing a chemical detection solution in accordance with the present disclosure, (ii) providing a fibrous substrate, and (iii) impregnating the fibrous substrate with the chemical detection solution. In another embodiment, the method further includes sealing the substrate in a package. In alternate embodiments, the fibrous substrate can be impregnated with the chemical detection solution before the fibrous substrate is positioned in the package or after the fibrous substrate is positioned in the package and prior to the sealing of the substrate in the package. In one embodiment, the method further includes flushing the package with an inert gas, such as, for example; carbon dioxide or nitrogen gas after the substrate is positioned in the package and before the package is sealed to reduce the amount of oxygen gas within the package or to remove oxygen gas from the package prior to sealing.

In accordance with certain embodiments, the substrate can be fed from storage rolls onto a coating machine, where the explosive material detection solution is applied. In alternative embodiments, which are provided only as examples, the solution can be added by running the substrate through a trough of the solution or the solution can be added to the substrate by spraying the formula from a series of nozzles. In still other embodiments, individual towelettes or wipes may be packaged in sealed foil pouches or packages by a process in which sheets of laminated foil are fed into a machine that folds them into a small pouch and heat seals three sides to form an open envelope. Simultaneously; another conveyor line feeds the substrates into the pouch, while a liquid feed mechanism injects the solution into the envelope containing the towelettes or wipes. Once the solution is added, another heat sealer then closes the remaining side of the pouch to seal the impregnated substrate within the package in a ready-to-use form.

In another aspect of the disclosure, various methods for determining whether an explosive substance is present on an object or surface are contemplated. One such method includes providing a detection wipe fabricated from a fibrous substrate impregnated with a chemical detection solution in accordance with the present disclosure; contacting the detection wipe with the surface; observing whether the detection wipe exhibits a change in color; and determining whether the explosive substance is present on the surface based on whether the detection wipe exhibits a color change. The detection wipe can have a variety of characteristics and features in accordance with the embodiments described herein. Another method of determining whether an explosive substance is present on a surface that is contemplated by this disclosure includes providing a detection wipe fabricated from a fibrous substrate; contacting the detection wipe with the surface; then spraying a chemical detection solution in accordance with the present disclosure onto the wipe; and determining whether the explosive substance is present on the surface based on whether the detection wipe exhibits a color change. Each of the substrate and the chemical detection solution in this embodiment can have a wide variety of characteristics and features in accordance with the embodiments described herein.

As described above, in one embodiment the explosive substance being detected is a nitrogen based explosives. In another embodiment, the explosive substance being detected is a nitrogen based explosives and the chemical detection solution includes a carrier fluid and Griess reagents. In yet another embodiment, the explosive substance being detected is a nitrogen based explosives and the chemical detection solution includes sulfanilamide and an ethylenediamine dihydrocholoride compound. In still another embodiment, the explosive substance being detected is a nitrogen based explosives and the chemical detection solution includes dimethyl sulfoxide, methanol, tetrabutylammonium hydroxide, sulfanilamide, ethylenediamine dihydrochloride and phosphoric acid.

In another embodiment, the explosive substance being detected is hydrogen peroxide. In another embodiment, the explosive substance being detected is hydrogen peroxide and the chemical detection solution includes a carrier fluid and a redox color indicating agent. In another embodiment, the explosive substance being detected is hydrogen peroxide, the redox color indicating agent comprises diphenylamine and the chemical detection solution includes ferric ions. In yet another embodiment, the explosive substance being detected is hydrogen peroxide, the redox color indicating agent comprises diphenylamine, the chemical detection solution includes ferric ions and the chemical detection solution includes an acidic carrier fluid.

Various processes; methods, compositions and devices of the present disclosure are further demonstrated in the following examples. These examples are illustrative only and are not intended to limit or preclude other embodiments of the present invention.

Example 1: Preparation and Use of a Hydrogen Peroxide Based Explosive Detection Wipe An illustrative absorbent nonwoven substrate wipe for detecting a peroxide based explosive material was fabricated as follows:

A first solution was prepared by mixing 7.4% dimethyl sulfoxide, 6.0% isopropyl alcohol, 0.5% diphenylamine and 86.0% sulfuric acid (50% solution), all by weight.

The first solution was then combined at a 1:1 ratio, by volume, with a second solution made by mixing 98.4% dipropylene glycol dimethyl ether, 0.8% ferric chloride and 0.073% hydrochloric acid (30% solution), all by weight to provide a chemical detection solution.

A hydroentangled and calendered nonwoven absorbent wipe obtained from Suominen Nonwovens (Bethune, S.C.) was impregnated with the final solution.

After fabrication, the wipe was contacted with hydrogen peroxide (also referred to herein as "peroxide"), which is a known explosive substance (i.e., is used to make certain explosives). Upon contact with the peroxide, the wipe quickly turned to an intense blue violet coloration, indicating the presence of the hydrogen peroxide.

In the presence of the peroxide, the $Fe^{3+}$ species in the chemical detection solution catalyzed the decomposition of the peroxide, thereby producing, among other things, reduced $Fe^{2+}$, while the $Fe^{2+}$ further reacted with the peroxide and oxidized to $Fe^{3+}$. In the presence of the redox indicator diphenylamine, the redox process turned the color indicator from clear (oxidized form) to color (reduced form). The end point was marked with an intense blue violet coloration. The reduction potential value of the system was $E°_{red}=+0.76V$, which was noted as being very near to the ferrous-ferric system ($E°_{red}=+0.77V$).

Regarding the chemistry behind the color change, since the wipe contained $Fe^{3+}$, sulfuric acid, hydrochloric acid and diphenylamine, when the wipe was exposed to the material containing $H_2O_2$, the $Fe^{3+}$ catalyzed the decomposition of the $H_2O_2$ into $H_2O$. As a result, it reduced $Fe^{3+}$ to $Fe^{2+}$ (among other species), which in this acidic medium and in the presence of $H_2O_2$, generated a Fenton's reagent. As is shown within the chemical reactions listed below, those of skill in the art will understand and appreciate that a Fenton's reagent is a solution that is formed by reaction of $Fe^{2+}$ and hydrogen peroxide. That is, $Fe^{2+}$ is oxidized to $Fe^{3+}$ by hydrogen peroxide to form a hydroxyl radical and a hydroxyl anion. $Fe^{3+}$ is then reduced back to $Fe^{2+}$ by the same hydrogen peroxide to a peroxide radical and a proton.

$$Fe^{3+}+H_2O_2 \rightarrow Fe^{2+}+HO_2 \cdot +H^+ \quad (1)$$

$$Fe^{2+}+H_2O_2 \rightarrow Fe^{3+}+{}^-OH+HO \cdot \quad (2)$$

$$HO_2 \cdot \leftrightarrow H^+ + O_2 \cdot^- \quad (3)$$

$$Fe^{3+}+HO_2 \rightarrow Fe^{2+}+H^++O_2 \quad (4)$$

The diphenylamine in the wipe operates as the redox color indicating agent that is responsible for generating the color species that resulted in the observed color change. The chemical reaction that took place is shown below. As those of skill in the art will understand and appreciate, the action of diphenylamine (I) as a redox color indicator depends upon its oxidation first into colorless diphenylbenzidine (II), which becomes the operative indicator in the solution and is reversibly further oxidized to diphenylbenzidine violet (III).

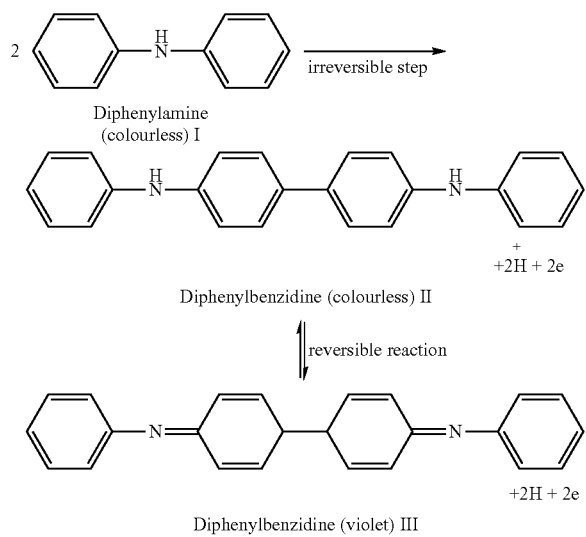

Example 2: Double Blind Study of Peroxide Based Explosive Detection Wipes

A double blind test was performed to evaluate the accuracy with which hydrogen peroxide based explosive detection wipes made as described in Example 1 identify the presence of hydrogen peroxide on test surfaces.

Set-Up

Thirty (30) human test subjects were recruited to conduct this study. The experiment was performed in a controlled setting, isolated from laboratories or other means of contamination. Numbered stickers, numbered from one (1) to thirty (30) were prepared to ensure that the test subjects were kept in order.

Several sets of thirty (30) test cards were prepared so that multiple trials could be run in the same session. The test cards consisted of a piece of construction paper with a smaller, white card in the middle, the latter having been contacted with a peroxide or nitrate-containing substance or nothing at all.

Procedure

The thirty (30) subjects were randomly divided into three (3) groups of ten (10) subjects, referred to herein as "primary groups," Each primary group was dubbed "A," "B," or "C." Each subject was given a test card and instructed to not touch the smaller, white card in the center as doing so could skew the results of the test. Each subject also was given a primary group card with either "A," "B," or "C" written on it, depending upon the primary group the subject was randomly placed in, and each subject was instructed to keep the primary group cards concealed until the final station.

Subjects in primary group A were given cards that had been in contact with a nitrate-containing substance. Subjects in primary group B received cards that had not come into contact with any substance. Subjects in primary group C receive cards that had come into contact with peroxide-containing compounds. Neither the subjects nor the persons recording results (test operators) were informed which primary group had which type of sample. The only person who knew which card the subjects received was the person who passed them out, who had no further role in the double blind study.

Out of the thirty (30) subjects a random number generator was used to form a first group of ten (10), referred to herein as a "secondary group," which was a random mixture of subjects from all three primary groups. A test operator at a first station assigned an order to the ten (10) subjects in the secondary group and dispensed a numbered sticker to each test subject so that the exact order was maintained within the secondary group throughout the trial. This process was then repeated using the random number generator to form a second secondary group of ten (10) subjects from the remaining twenty (20) subjects, and was again repeated with the remaining ten (10) subjects, who formed a third secondary group, thereby randomly generating three secondary groups.

The first secondary group of ten (10) subjects then proceeded to the second station, one at a time in chronological order, where another test operator tested the subject's card by wiping a hydrogen peroxide based explosive detection wipe made in accordance with Example 1 over the card. Yet another test operator logged the results on data sheets, the result from each card tested being a positive or a negative result. A positive result was logged for a given card, indicating that the card was determined to contain peroxide, if the swiped area turned blue violet after the card was wiped. A negative result was logged for a given card, indicating that the card was determined to not contain peroxide, if the swiped area did not change color after the card was wiped. Once results were logged for a given card, the card was discarded.

The subject then proceeded to the third and final station, where another test operator logged the subject's order and group information. At this station, the subject revealed his or her primary group card to the test operator, which information also was recorded by the test operator. The subject then re-concealed his or her primary group card, returned to his or her respective secondary group, received a new test card, and waited to be called again.

After a sufficient amount of data (more than 200 test points) was acquired, testing ended. Data from the testing station and group station were compared by an independent third party, and the data was analyzed to measure the accuracy of the hydrogen peroxide based explosive detection wipes to accurately indicate whether a hydrogen peroxide residue was present on the respective test cards.

| Sample Data | | | |
|---|---|---|---|
| Sample of Data Collected at Testing Station | | Sample of Data Collected at Group Station | |
| Subject | Peroxide | Subject | Group |
| 1 | + | 1 | C |
| 2 | − | 2 | A |
| 3 | + | 3 | C |
| 4 | − | 4 | B |
| 5 | − | 5 | A |

The sample data displayed above demonstrates how the two data sets collected as described above were used to verify whether or not results logged at the testing station were accurate by comparing them to the group station data. For example, in the above sample data, subjects 1 and 3 tested positive for peroxide and were from Group C, which would be a correct result. Subjects 2 and 5, which were from Group A, and subject 4, which was from Group B, tested negative for peroxide, which also would be correct results.

In order to quantify the results, each correct result was given a value of 100 and each incorrect result was given a value of 0. These values were then averaged once all the results were determined. This average represents the percent accuracy of the hydrogen peroxide based explosive detection wipes.

Results

The results of the double blind test described above showed that the detection wipes tested were 100% accurate in identifying the presence of hydrogen peroxide, with no false positives when the wipe was used to wipe test cards that included nitrogen residues and test cards that included no hydrogen peroxide or nitrogen residues on the test surfaces.

Example 3: Preparation and Use of a Nitrogen Based Explosive Detection Wipe

An illustrative absorbent nonwoven substrate wipe for detecting a nitrogen based explosive material was fabricated as follows:
A chemical detection solution was prepared by mixing dimethyl sulfoxide, methanol, tetrabutylammonium hydroxide, sulfanilamide, ethylenediamine dihydrochloride and phosphoric acid to provide a chemical detection solution having these ingredients in the following proportions, by weight: about 74% dimethyl sulfoxide, 9% methanol, 3% tetrabutylammonium hydroxide, 6% sulfanilamide, 0.2% ethylenediamine dihydrochloride and 8% phosphoric acid having a Molarity of about 85%.
A hydroentangled and calendered nonwoven absorbent wipe obtained from Suominen Nonwovens (Bethune, S.C.) was impregnated with the chemical detection solution.

After fabrication, the wipe was contacted with a nitrate-containing substance, which is known to be present in "gunshot residue". Upon contact with the nitrate-containing substance, the wipe quickly turned to an intense magenta color, indicating the presence of nitrite ions or nitro functional groups.

Generation of the color species that resulted in the observed color change occurred by a series of chemical reactions similar to the Griess reaction shown below.

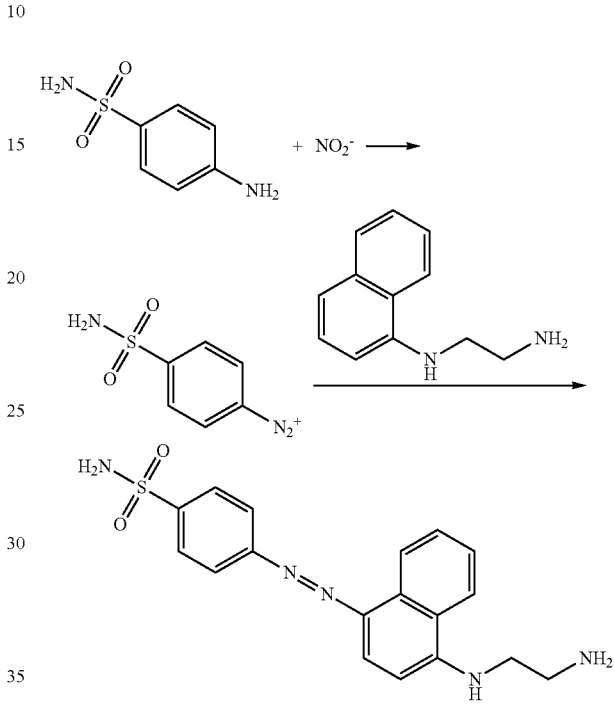

In this reaction, the sulfanimide reacts with a nitrite ion donated by the nitrate-containing substance to produce a diazonium salt. The diazonium salt then reacted with ethylenediamine dihydrochloride (represented in the Griess reaction shown above as N-(1-Naphthyl)ethylenediamine) to produce an azo dye (represented the Griess reaction shown above as N-alpha-naphtyl-ethylenediamine), which produces the magenta color.

Example 4: Double Blind Study of Nitrogen Based Explosive Detection Wipes

A double blind test was performed to evaluate the accuracy with which nitrogen based explosive detection wipes made as described in Example 3 identify the presence of nitrogen based explosives on test surfaces. The Set-Up and Procedure used for this double blind test are the same as the Set-Up and Procedure described in Example 2 except for the following differences:

The test operator at the second station tested the subject's card by wiping a nitrogen based explosive detection wipe made in accordance with Example 3 over the card. A positive result was logged by another test operator for a given card, indicating that the card was determined to contain a nitrate-containing substance, if the swiped area turned magenta after the card was wiped. A negative result was logged for a given card, indicating that the card was determined to not contain a nitrate-containing substance, if the swiped area did not change color after the card was wiped.

After a sufficient amount of data (more than 200 test points) was acquired, testing ended. Data from the testing station and group station were compared by an independent third party, and the data was analyzed to measure the accuracy of the nitrogen based explosive detection wipes to accurately indicate whether a nitrate-containing residue was present on the respective test cards.

| Sample Data | | | |
|---|---|---|---|
| Sample of Data Collected at Testing Station | | Sample of Data Collected at Group Station | |
| Subject | Nitrate | Subject | Group |
| 1 | + | 1 | C |
| 2 | − | 2 | A |
| 3 | + | 3 | C |
| 4 | − | 4 | B |
| 5 | − | 5 | A |

The sample data displayed above demonstrates how the two data sets collected as described above were used to verify whether or not results logged at the testing station were accurate by comparing them to the group station data. For example, in the above sample data, subjects 1 and 3 tested positive for a nitrate-containing substance and were from Group C, which would be a correct result. Subjects 2 and 5, which were from Group A, and subject 4, which was from Group B, tested negative for a nitrate-containing substance, which also would be correct results.

Results

The results of the double blind test described above showed that the detection wipes tested were greater than 99% accurate in identifying the presence of a nitro- or nitrate-containing substance.

While exemplary embodiments incorporating the principles of the present application have been disclosed herein, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method actions, processes, and operations described herein are not to be construed as necessarily requiring their performance in the particular order discussed or illustrated, unless specifically identified as an order of performance. It is also to be understood that additional or alternative actions or operations may be employed.

Although the terms first, second, third, etc, may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed herein could be termed a second element, component, region, layer or section without departing from the teachings of the example embodiments.

What is claimed is:

1. A wipe for detecting the presence of an explosive substance, comprising:
    a fibrous substrate; and
    a chemical detection solution impregnated into the substrate, the chemical detection solution including a carrier fluid and a combination of reagents operable to undergo a chemical reaction or a series of chemical reactions to produce a compound having a visible color when the solution contacts the explosive substance;
    wherein said impregnated substrate is contained within a sealed package; and
    wherein said impregnated substrate is configured to be removed from the sealed package and wiped over a surface for detection of the presence or absence of an explosive substance on the surface.

2. The wipe of claim 1 wherein the fibrous substrate comprises a plurality of fibers selected from the group consisting of cellulose, polyamides, polyesters, polyethylenes, polypropylenes, polyacrylics, cellulose acetate, polylactic acid, silk, wool, glass, polyaramids, and combinations thereof.

3. The wipe of claim 1 wherein the fibrous substrate is a nonwoven material having multiple layers formed from fibers selected from the group consisting of polyolefin, polypropylene, polyethylene, ethylene copolymers and propylene copolymers.

4. The wipe of claim 1 wherein the fibrous substrate is an absorbent nonwoven material formed from a blend of spunbond fibers.

5. The wipe of claim 4 wherein the blend of spunbond fibers is selected from the group consisting of polypropylene, polyester and wood pulp.

6. The wipe of claim 1 wherein the combination of reagents includes Griess reagents.

7. The wipe of claim 6 wherein the Griess reagents include sulfanilamide and an ethylenediamine dihydrochloride.

8. The wipe of claim 6 wherein the chemical detection solution has a pH of from about 2.5 to about 5.0.

9. The wipe of claim 6 wherein the carrier fluid includes at least one solvent, at least one base and at least one acid.

10. The wipe of claim 9 wherein the at least one solvent comprises dimethylsulfoxide and methanol.

11. The wipe of claim 9 wherein the at least one base comprises tetrabutylammonium hydroxide.

12. The wipe of claim 9 wherein the at least one acid comprises phosphoric acid.

13. The wipe of claim 1 wherein the chemical detection solution includes dimethyl sulfoxide, methanol, tetrabutylammonium hydroxide, sulfanilamide, ethylenediamine dihydrochloride and phosphoric acid.

14. The wipe of claim 1 wherein the chemical detection solution comprises from about 65% to about 85% dimethyl sulfoxide, from about 4% to about 13% methanol, from about 1% to about 5% tetrabutylammonium hydroxide, from about 3% to about 9% sulfanilamide, from about 0.1% to about 0.3% ethylenediamine dihydrochloride and from about 5% to about 10% phosphoric acid having a Molarity of at least 70%, all by weight.

15. A method of fabricating an explosive substance detection wipe, the method comprising:
providing a chemical detection solution that includes a carrier fluid and Griess reagents;
providing a fibrous substrate;
impregnating the fibrous substrate with the chemical detection solution to provide an impregnated substrate; and
placing the impregnated substrate in a sealed package;
wherein said impregnated substrate is configured to be removed from the sealed package and wiped over a surface for detection of the presence or absence of an explosive substance on the surface.

16. The method of claim 15 wherein said providing a chemical detection solution comprises mixing at least one solvent, at least one base and at least one acid with sulfanilamide and ethylenediamine dihydrochloride to form a chemical detection solution.

17. The method of claim 16 wherein the at least one solvent comprises dimethyl sulfoxide and methanol.

18. The method of claim 16 wherein the at least one base comprises tetrabutylammonium hydroxide.

19. The method of claim 16 wherein the at least one acid comprises phosphoric acid.

20. The method of claim 16 wherein the chemical detection solution comprises from about 65% to about 85% dimethyl sulfoxide, from about 4% to about 13% methanol, from about 1% to about 5% tetrabutylammonium hydroxide, from about 3% to about 9% sulfanilamide, from about 0.1% to about 0.3% ethylenediamine dihydrochloride and from about 5% to about 10% phosphoric acid having a Molarity of at least 70%, all by weight.

21. The method of claim 15 wherein the fibrous substrate comprises a nonwoven material having multiple layers formed from polyolefin, polypropylene, polyethylene, ethylene copolymers and propylene copolymers.

22. The method of claim 15 wherein the fibrous substrate comprises an absorbent nonwoven material formed from a blend of spunbond fibers selected from the group consisting of polypropylene, polyester and wood pulp.

23. A method of determining whether an explosive substance is present on a surface, comprising:
providing a detection wipe fabricated from a fibrous substrate impregnated with a chemical detection solution that includes a carrier fluid and Griess reagents;
wiping the surface with the impregnated substrate of the detection wipe, wherein the impregnated substrate is removed from a packaging containing the detection wipe;
observing whether the detection wipe exhibits a change in color; and
determining whether the explosive substance is present on the surface based on whether the detection wipe exhibits a color change.

24. The method of claim 23 wherein the fibrous substrate comprises an absorbent nonwoven material formed from a blend of spunbond fibers selected from the group consisting of polypropylene, polyester and wood pulp.

25. The method of claim 23 wherein the chemical detection solution comprises dimethyl sulfoxide, methanol, tetrabutylammonium hydroxide, sulfanilamide, ethylenediamine dihydrochloride and phosphoric acid.

26. A method of detecting a nitrate ester compound, a nitroamine compound or other nitro compound on a surface, comprising:
providing a detection wipe fabricated from a fibrous substrate impregnated with a chemical detection solution that includes a carrier fluid and Griess reagents;
wiping the surface with the impregnated substrate of the detection wipe, wherein the impregnated substrate is removed from a packaging containing the detection wipe;
observing whether the detection wipe exhibits a change in color; and
determining whether a nitrate ester compound, a nitroamine compound or other nitro compound is present on the surface based on whether the detection wipe exhibits a color change.

27. The method of claim 26 wherein the chemical detection solution includes dimethyl sulfoxide, methanol, tetrabutylammonium hydroxide, sulfanilamide, ethylenediamine dihydrochloride and phosphoric acid.

* * * * *